(12) United States Patent
Fleischer et al.

(10) Patent No.: US 10,123,734 B2
(45) Date of Patent: *Nov. 13, 2018

(54) APPLIANCE FOR PEOPLE WITH REDUCED SENSE OF TOUCH OR DISABLED PEOPLE

(71) Applicant: REQBO APS, Aarhus (DK)

(72) Inventors: Jesper Fleischer, Hojbjerg (DK); Anders Geert Jensen, Risskov (DK)

(73) Assignee: REQBO APS, Aarhus N (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,989

(22) Filed: May 1, 2017

(65) Prior Publication Data

US 2017/0231551 A1    Aug. 17, 2017

Related U.S. Application Data

(63) Continuation of application No. 14/433,597, filed as application No. PCT/IB2013/002919 on Oct. 7, 2013, now Pat. No. 9,636,045.

(30) Foreign Application Priority Data

Oct. 5, 2012   (DK) .................................. 2012 70605

(51) Int. Cl.
   *G08B 13/14*      (2006.01)
   *A61B 5/00*       (2006.01)
   (Continued)

(52) U.S. Cl.
   CPC ............ *A61B 5/447* (2013.01); *A61B 5/1036* (2013.01); *A61B 5/6807* (2013.01);
   (Continued)

(58) Field of Classification Search
   CPC ..... A61B 5/1036; A61B 5/1038; A61B 5/447; A61B 5/6807; A61B 5/6892;
   (Continued)

(56) References Cited

U.S. PATENT DOCUMENTS 5,471,405 A   11/1995  Marsh
5,500,635 A   3/1996   Mott
(Continued)

FOREIGN PATENT DOCUMENTS

DE   102007028467   12/2008
WO   200180678      11/2001
WO   2004073577     9/2004

OTHER PUBLICATIONS

International Search Report in International Application No: PCT/IB2013/002919; dated Apr. 24, 2014. International Publication No. WO 2014/060844; International Publication Date: Apr. 24, 2014.
(Continued)

*Primary Examiner* — Hung T Nguyen
(74) *Attorney, Agent, or Firm* — Dave Law Group LLC; Raju Dave

(57) ABSTRACT

Disclosed herein are devices, methods and systems for monitoring and detection of pressure on a part of a body of a user. In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed.

20 Claims, 8 Drawing Sheets

(51) Int. Cl.
*A61B 5/103* (2006.01)
*G08B 21/18* (2006.01)

(52) U.S. Cl.
CPC ............ *A61B 5/6892* (2013.01); *A61B 5/742* (2013.01); *A61B 5/7405* (2013.01); *A61B 5/7455* (2013.01); *G08B 21/182* (2013.01); *A61B 2562/029* (2013.01); *A61B 2562/0247* (2013.01); *A61B 2562/0271* (2013.01)

(58) Field of Classification Search
CPC ............ G08B 21/18247; G08B 13/14; G06K 19/073; G06K 19/077
USPC .... 340/539.12, 572.4, 572.8, 626, 665, 666; 73/172, 862.041; 128/736, 779; 235/375, 376, 487, 492
See application file for complete search history.

(56) References Cited

U.S. PATENT DOCUMENTS

| | | | |
|---|---|---|---|
| 5,642,096 A | 6/1997 | Leyerer | |
| 6,430,843 B1 | 8/2002 | Potter | |
| 7,726,206 B2 | 6/2010 | Collins et al. | |
| 8,185,181 B2 | 5/2012 | Feldman et al. | |
| 8,384,551 B2 | 2/2013 | Ross et al. | |
| 9,050,041 B2 | 6/2015 | Feldman et al. | |
| 2004/0074966 A1* | 4/2004 | Holzer | A43B 3/0005 235/385 |
| 2005/0261609 A1* | 11/2005 | Collings | A43B 3/0005 600/592 |
| 2006/0248750 A1 | 11/2006 | Rosenberg | |
| 2007/0173903 A1* | 7/2007 | Goren | A61N 1/32 607/49 |
| 2009/0135001 A1 | 5/2009 | Yuk | |
| 2009/0137933 A1* | 5/2009 | Lieberman | A61B 5/1036 600/595 |
| 2009/0192364 A1 | 7/2009 | Voto | |
| 2010/0283630 A1* | 11/2010 | Alonso | H04Q 9/00 340/870.11 |
| 2011/0054359 A1 | 3/2011 | Sazonov et al. | |
| 2011/0214501 A1 | 9/2011 | Ross et al. | |

OTHER PUBLICATIONS

English Abstract of DE 102007028467; Applicant: Polyic Gmbh & Co. KG. Publication Date: 2009 (English Abstract from Derwent World Patents Index) (7 pages).
International Preliminary Report on Patentability dated Apr. 7, 2015 in International Application PCT/IB2013/002919.
International Preliminary Report on Patentability dated Mar. 31, 2015 in International Application PCT/US2013/062719.

* cited by examiner

APPLIANCE FOR PEOPLE WITH REDUCED SENSE OF TOUCH OR DISABLED PEOPLE

CROSS REFERENCE

This application is a continuation of U.S. patent application Ser. No. 14/433,597, filed Apr. 3, 2015, now U.S. Pat. No. 9,636,045, which claims priority to PCT/IB2013/002919, filed on Oct. 7, 2013, which in turn claims the benefit of priority from Denmark patent application no. PA 2012 70605, filed on Oct. 5, 2012, all of which are herein incorporated by reference in their entireties.

TECHNICAL FIELD

This disclosure relates generally to monitoring and prevention of health related conditions of a subject, and in particular, to a method and apparatus for monitoring and preventing pressure ulcers.

BACKGROUND ART

Pressure ulcers, also called bed sores, are a major health issue. Bedridden patients, wheelchair bound patients, people with limited mobility or reduced sensation of touch, e.g. those suffering from diabetic peripheral neuropathy, have high risk of developing pressure ulcers (PUs). PUs can develop quickly and are painful for the patient. They are generally resistant to known medical therapy and, are often very difficult to heal. PUs can cause reduced anatomical or functional integrity in patients and can, occasionally lead to life threatening complications. Care for patients suffering from PUs is often time consuming, personnel intensive and expensive. Once developed, PUs increased hospital stay, imposing enormous burden on the healthcare system and diverting precious personnel resources that may be allocated for other patients.

Either static or long-term dynamic or punctual load, which allows pressure marks on an insensitive or passive area on the body, can lead to pressure ulcers if not taken care of in time. Such occurrences of pressure can occlude blood supply to parts of the body leading to tissue ischemia. If such pressure is not relieved over a long period of time tissue ischemia can lead to permanent cell damage causing pressure ulcers. The person with normal sensation and mobility would be immediately alerted while the person without sensation—without knowing it—allows repeated high pressure and/or static load on the same small place on the body. This can create sores or precursors thereof.

For example, patients suffering from diabetic peripheral neuropathy have reduced sensation in their extremities and may not sense a wound or skin damage to their hands and/or feet. In such patients, a wound or skin damage on the foot can occur without detection, and the condition can lead to complications such as severe infection, slow healing wounds and risk of amputation. Therefore it becomes important for staff at the hospital or nursing home to constantly monitor vulnerable areas of the body and especially observe pressure related alteration of the skin that may be precursors of pressure ulcer.

So far, the most effective care for an at-risk patient is to relieve the pressure which, in hospitals, is commonly done by periodically repositioning bed-bound patients. Because every patient has levels of risk of occurrence of PUs depending on factors such as age, sex, disease conditions, blood pressure, nutrition, etc., some patients may need more frequent repositioning than others. Determining the schedule for repositioning is difficult may yet be unable to prevent occurrence of PUs.

Devices for monitoring patients to prevent and/or detect PUs generally include an array of pressure sensors placed in close proximity to parts of a patient's body that are at a higher risk of forming PUs. The pressure sensors record pressure on the at-risk parts and provide the data to a caregiver so that the caregiver may relive the excess pressure from particular parts by suitably repositioning the patient. However, in generally, such devices are expensive and do not, by themselves, absorb or relieve pressure. For example, it would be rather expensive to change a sock having an array of pressure sensors on a daily basis. Furthermore, there may be problems with machine washing and/or autoclaving, as the connection (e.g., a cable) from the sensor to the electronics may not be adequately protected. Moreover, such devices technologies fail to utilize pressure relieving and shock absorbing areas of the patient's body that could otherwise be used. Furthermore, the dimensions of sensor array devices and spatial constraints for placing these arrays in proximity to a certain body part limit the available locations for placement of such devices. For example, while it may be suitable to use such devices on a mattress or a sheet, it may not work in a shoe or a sock because of the limited space available for placing the sensor without chaffing the user's foot.

SUMMARY

In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed. The one or more sensors adapted to measure changes in pressure in the one or more sacs.

In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed. Changes in pressure in the one or more sacs are measured using one or more sensors in communication with the one or more sacs.

In an embodiment, a system includes (i) a device having a substrate having a contact surface for contacting a user and one or more fluidic material filled sacs associated with the contact surface of the substrate, (ii) a controller configured to transmit and/or receive radio frequency signals to and from the one or more sensors corresponding to the measured changes in pressure, and (iii) a user feedback device in communication with the controller, a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed. The user feedback device configured to provide an indication to a user based on the measured changes in pressure. Changes in pressure in the one or more fluidic material filled sacs are measured using one or more sensors in communication with the one or more fluidic material filled sacs.

In an embodiment, a method includes measuring pressure exerted by a portion of a subject's body on one or more sacs associated with a substrate having a contact surface for contacting with the portion of the subject's body to provide pressure information, and transmitting the pressure information to a receiving station. The pressure information indicates, using one or more of audio, visual, audiovisual or haptic signal.

BRIEF DESCRIPTION OF DRAWINGS

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein.

DETAILED DESCRIPTION

Figure 1:
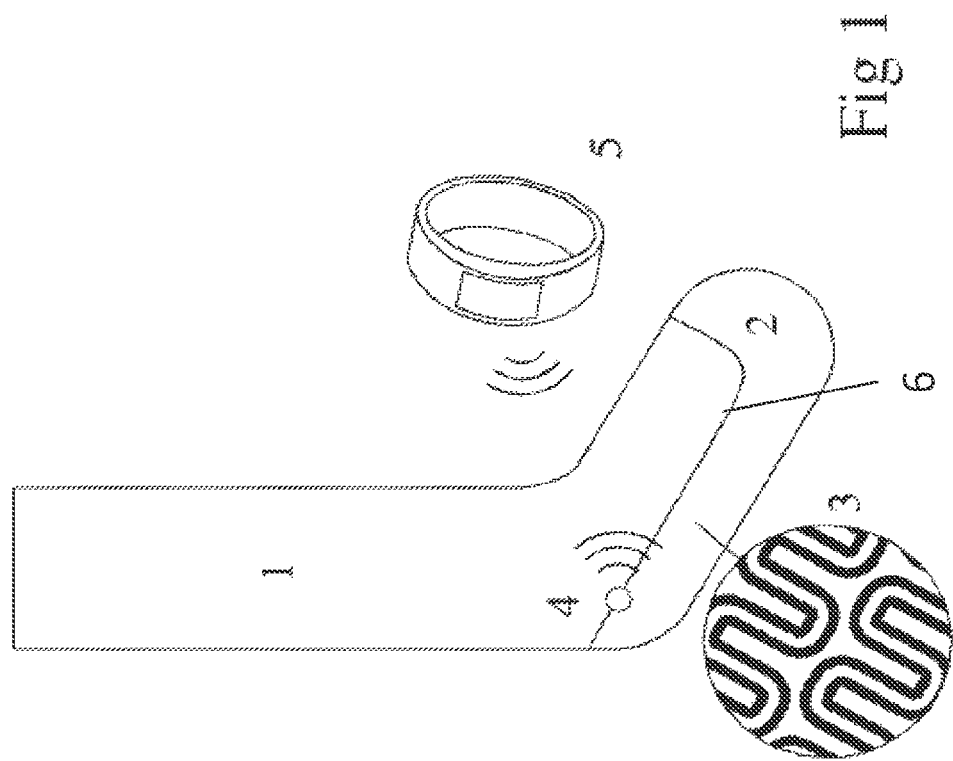
FIG. 1 depicts one embodiment of a pressure monitoring device incorporated in a sock, in accordance with the principles and aspects of the present disclosure.

Before the present methods and systems are described, it is to be understood that this disclosure is not limited to the particular processes, methods and devices described herein, as these may vary. It is also to be understood that the terminology used herein is for the purpose of describing the particular versions or embodiments only, and is not intended to limit the scope of the present disclosure which will be limited only by the appended claims. Unless otherwise defined, all technical and scientific terms used herein have the same meanings as commonly understood by one of ordinary skill in the art.

It must also be noted that as used herein and in the appended claims, the singular forms "a", "an", and "the" include plural reference unless the context clearly dictates otherwise. Thus, for example, reference to a "sensor" is a reference to one or more sensors and equivalents thereof known to those skilled in the art, and so forth. Nothing in this disclosure is to be construed as an admission that the embodiments described in this disclosure are not entitled to antedate such disclosure by virtue of prior invention. As used in this document, the term "comprising" means "including, but not limited to."

Disclosed herein are devices, methods and systems for monitoring and detection of pressure on a part of a body of a user. In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed.

As used herein, the term "sensor" refers to a device that measures a physical quantity and converts it into a signal which can be read by an observer or an instrument. In an embodiment, a pressure sensor may be a device for measuring a pressure and converting it into an electrical signal that can be can be read using an electronic instrument. In such embodiment, a change in pressure results in an electrical signal or a change in an electrical signal that is correlated with the change in pressure, thereby providing a measure of the change in pressure. The pressure measured by a pressure sensor may be absolute pressure or relative pressure, e.g., pressure relative to atmospheric pressure.

Likewise, a temperature sensor may convert a temperature or a change in temperature into an electrical signal and a humidity sensor may convert humidity or a change in humidity into an electrical signal. The humidity measured by a humidity sensor may be absolute humidity or relative humidity. In various embodiments, a sensor may need to be calibrated to provide a meaningful measure. In some embodiments, a sensor may not convert a measurement into an electrical signal.

Examples of pressure sensors include, but are not limited to, (i) strain gauges wherein stretching of a lead wire leads to a measurable change in resistance of the lead wire; (ii) piezoresistive sensors wherein resistance of the sensor material is sensitive to deformations and displacements; (iii) capacitive sensors wherein capacity of the sensor is measurably changed because a deformation causes a change in the distance between the plates and/or the overlapping area of the plates; and the like.

As used herein, the term "fluidic material" refers to a gas, a liquid, a gel, or a pressure absorbing solid, e.g., foam. Examples of fluidic material include, but are not limited to, ethylene vinyl acetate, rubber, silicone rubber, Polyurethane rubber (PUR), neoprene, or air. Terms "fluidic material sac," or "fluidic material filled sac," or "sac filled with fluidic material" are used interchangeably and refer to a cavity disposed in a substrate, the cavity being filled with a fluidic material such as a gas, a liquid, a gel, or a pressure absorbing solid. The fluidic material filled sac can be made from a textile fabric material such as, for example, nylon, spandex, silk, wool, cotton, polyester, and the like, or a combination thereof. In other embodiments, the fluidic material filled sac can be made from a pliable material such as, for example, rubber, plastic, silicone, neoprene and the like, or any combination thereof.

In some embodiments, the fluidic material in the fluidic material filled sac is chosen such that excess pressure at a localized area of the sac is redistributed throughout the sac by displacement of the fluidic material, thereby relieving the pressure from the localized area. Furthermore, such a sac filled with a fluidic material enables absorption and dissipation of sudden changes in pressure, thereby acting as a shock-absorber. As such, a sac filled with a fluidic material described herein can act as a pressure-relieving and shock-absorbing device for a user.

In many embodiments, a plurality of fluidic material filled sacs in fluidic material conducting communication with each other to form a network may be used. The fluidic material fluidic material in such a network of fluidic material filled sacs may redistribute pressure from a small localized area over a larger area, thereby relieving excess localized pressure. Furthermore, such a network also enables absorption and dissipation of sudden changes in pressure, thereby acting as shock-absorber. As such, a network of sacs filled with a fluidic material described herein can act as a pressure-relieving and shock-absorbing device for a user.

As used herein, the term "user" refers to a subject, human or animal, that uses the device or system disclosed herein. A user may be a person at risk for pressure ulcers such as, for example, a bed-ridden subject, a patient of diabetic peripheral neuropathy, a wheel-chair bound person, and the like. In some embodiments, a user may be a subject suffering from pressure ulcers.

FIG. 1 depicts one embodiment of a pressure monitoring device incorporated in a sock, in accordance with the principles and aspects of the present disclosure. Size of the sock 1 is adapted to the individual user, so it fits comfortably. A pillow-like region forms the substrate 2 and surrounds the underside and the front part of the foot of a user. Fluidic material filled sacs 3 are disposed in the pillow-like substrate and are configured to transmit the changes to various internal and external factors (e.g., pressure, temperature, humidity and the like) to one or more sensors 4 disposed on the substrate.

In some embodiments, substrate 2 is made of thin, flexible, resilient and elastic textile product. Examples of materials that may be used for making substrate 2 include, but are not limited to, nylon, spandex, silk, wool, cotton, polyester, and the like, or a combination thereof. Contact surface 6 is the surface of substrate 2 that engages or comes in contact with the user's foot. Suitable permeability for water vapour and bacteriostatic properties are desirable for the material of the contact surface so as to reduce risk of unwanted infections and for user comfort. Material of contact surface 6 can be natural or synthetic fibres.

Associated with contact surface 6 of substrate 2 is disposed one or more fluidic material filled sacs 3 configured such that the fluidic material is displaceable between different sacs by an action, e.g. movement of the foot, of the user contacting the contact surface. Such configuration allows for fluidic material pressure in the one or more sacs 3 to be redistributed so as to dissipate and relieve excess pressure from a localized portion of a user's body in contact with contact surface 6.

In various embodiments, fluidic material filled sacs 3 can be secured on portions of substrate 2 by means of thermoweld, bonding, molding, laminating, sewing or any other suitable mechanism. In an embodiment, fluidic material filled sacs 3 have a meandering pattern. In some embodiments, fluidic material filled sacs 3 may be made of silicone, or similar compressible material that is capable of redistributing pressure. In an embodiment, a surface of the fluidic material filled sacs coincides with the contact surface.

One or more sensors 4 may be disposed in communication with one or more fluidic material filled sacs 3. The sensors 4 may include, for example, pressure sensors, temperature sensors, humidity sensors, blood pressure sensors, and the like. In one embodiment, one or more pressure sensors are disposed and secured inside one of fluidic material filled sacs 3. In another embodiment, one or more pressure sensors are disposed and secured on an outer surface of one of fluidic material filled sacs 3. In yet another embodiment, one or more pressure sensors are associated with contact surface 6 of substrate 2.

In some embodiments, one or more sensors 4 are connected to a transmitter (not shown) that can transmit the data measured by one or more sensors 4 from the measurement area to a remote receiver 5. In various embodiments, the transmitter may use communication technologies such as, for example, Radio Frequency communication (RF), Near Field Communication (NFC), Bluetooth, Bluetooth low energy (BLE), and the like.

In an embodiment, the transmitter is an RF transmitter. RF transmitters are widely used for uniquely identifying objects using radio frequency electromagnetic signals. Examples of uses of RF transmitter include, but are not limited to, inventory control, theft protection, monitoring tires pressure in cars, and the like. Typical RF transmitters use an RF Identifier (RFID) which consists of transmitter (tag) for transmitting a unique identifier and other data to RF Readers, which are configured to receive and decode data transmitted by the RFID. The tag is typically composed of an antenna and a circuit to control a microchip. In some embodiments, the tag's microchip and antenna may both be used for the measurement of pressure. An RF tag may be a passive tag or an active tag. A passive tag has no internal source of energy and therefore, may not require any maintenance. A passive RFID tag is activated only when sending a specific radio signal. At such time the tag "wakes up" and transmits a unique ID number and a characteristic measurable resistance which depends on the pressure of the material it is attached to.

In various embodiments, the RF transmitter may be disposed at a location where it is not obstructive to the user and does not create pressure points. For example, the RF transmitter may be glued to a sole or sewn into a sock. In some embodiments, remote receiver 5 may be, for example, a bracelet, a mobile phone, remote control or the like. Remote receiver 5, in some embodiments, may be configured to provide a feedback to the user and/or a caregiver attending to the user. The feedback system can be embodied with, e.g., colored light, to indicate when a foot is subjected to undesirable stresses.

Figure 7:
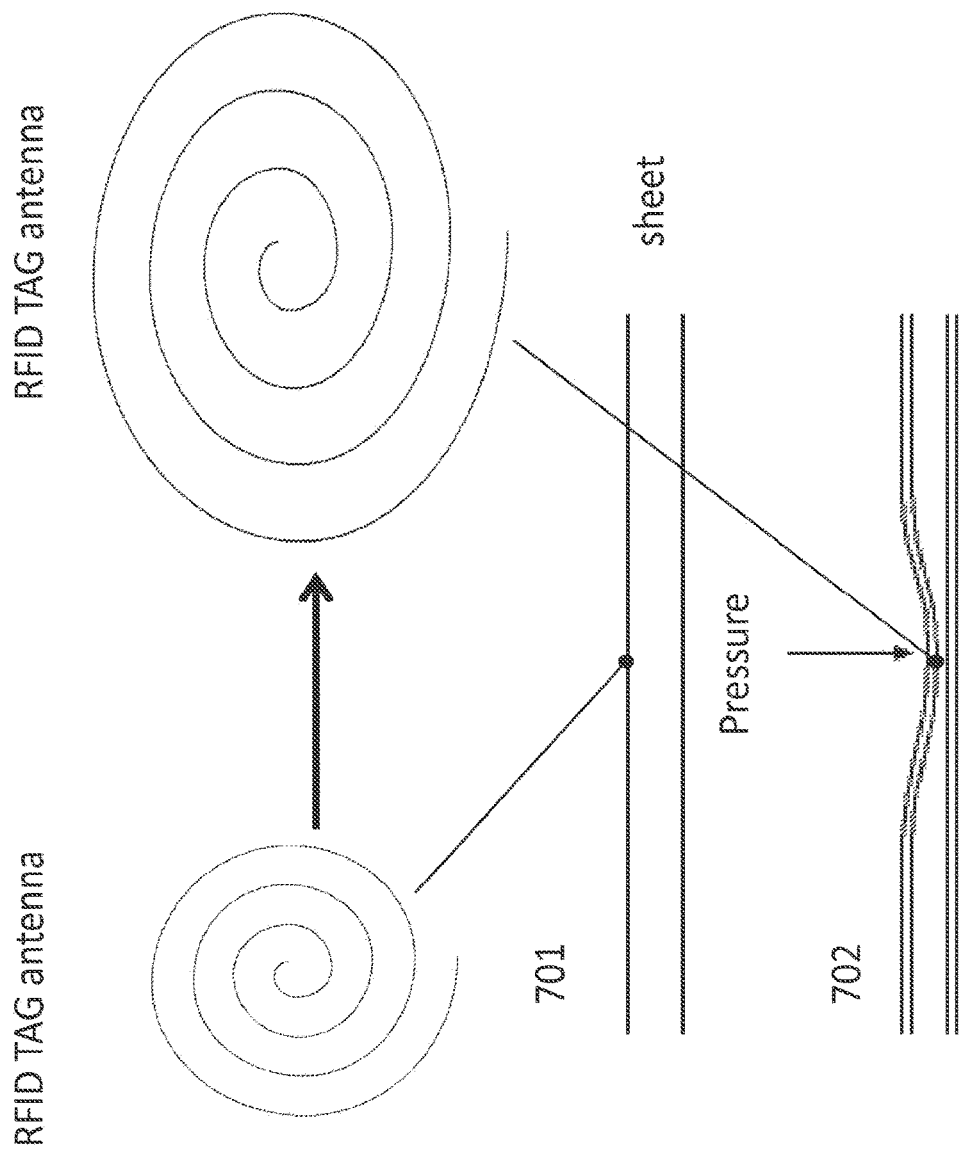
FIG. 7 depicts an embodiment with a radio frequency transmitter is also used a pressure sensor, in accordance with the principles and aspects of the present disclosure.

In various embodiments, a RF transmitter itself may act as a pressure sensor a described elsewhere herein (in reference to FIG. 7). In such embodiments, the RF transmitter may be placed directly at the measuring area, e.g. at one of fluidic material filled sacs 3 as a direct pressure sensor, or in proximity as an indirect pressure sensor where the pressure signal from one area is being transmitted to the sensor via one or more other areas.

In one embodiment fluidic material filled sacs 3 form a tree-like structure whereby different sacs are in fluidic material conducting communication with each other via the branches so that pressure changes can be transferred from a fluidic material filled sac in one area to one or more fluidic material filled sacs in another area via the branches. In some embodiments, fluidic material filled sacs 3 may be filled using a movable liquid or gel which, in addition to transferring the pressure changes, can also massage and support the blood circulation during operation. Such configuration provides the advantage that any excess pressure affecting the contact surface is distributed over a larger area, thereby minimizing its deleterious effects. The material in fluidic material filled sacs 3 can move, and can be used to measure the pressure or change in pressure using one of or more sensors 4. In embodiments with a transmitter, and a remote receiver, measurements of pressure or change in pressure are further transmitted to the remote receiver via the transmitter.

Figure 2:
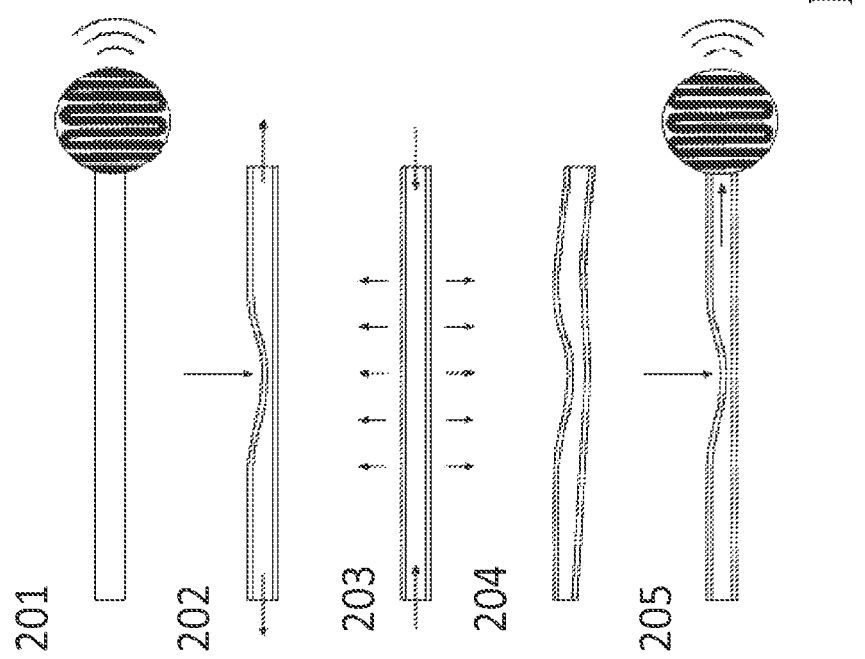
FIG. 2 depicts an illustrative schematic of response of a device subjected to a local compressive load, in accordance with the principles and aspects of the present disclosure.

FIG. 2 depicts an illustrative schematic of response of a device subjected to a local compressive load, in accordance with the principles and aspects of the present disclosure. 201 depicts a schematic drawing of fluidic material filled sac 3 is shown. 202 schematically depicts the effect of subjecting fluidic material filled sac 3 to a local compressive load. 203 schematically depicts how the local compressive load is quickly eliminated by the pressure being dispersed to the entire material. 204 schematically depicts that the material used to fill fluidic material filled sac 3 is resilient and can expand if necessary. 205 schematically depicts how the pressure changes (both static and dynamic changes) in the material in fluidic material filled sacs propagate to one or more sensors 4.

Figure 3:
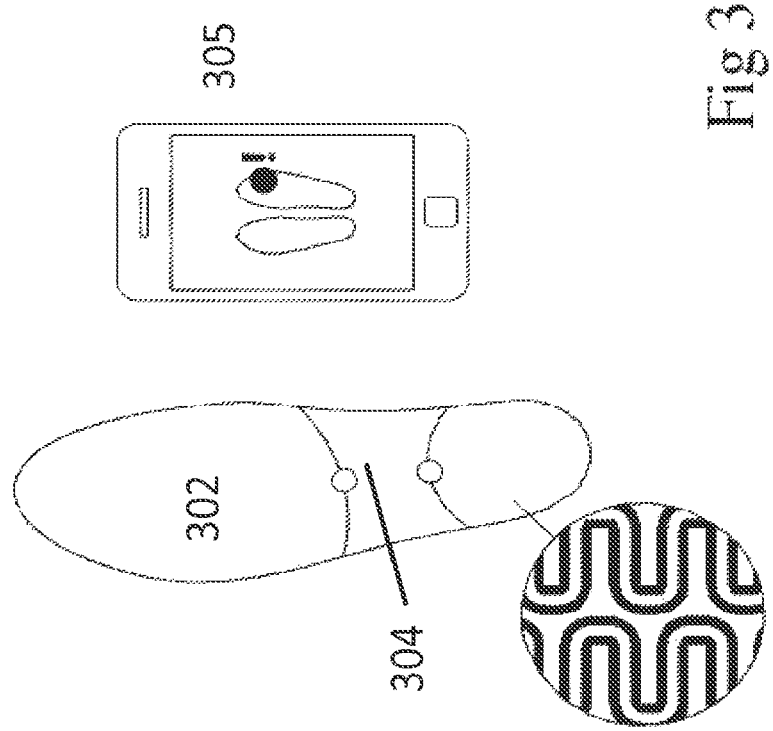
FIG. 3 depicts an embodiment of a pressure monitoring device incorporated in a shoe-sole is controlled using a smartphone, in accordance with the principles and aspects of the present disclosure.

FIG. 3 depicts an embodiment of a pressure monitoring device incorporated in a shoe-sole is controlled using a smartphone, in accordance with the principles and aspects of the present disclosure. The shoe sole 302 acts as the substrate. Sensors 304 are placed on the underside of the shoe sole. 305 schematically depicts an example of user interface for a remote receiver in the form of a smart-phone.

In various other embodiments, substrate may be an article in contact with a user's body. Examples of substrates include, but are not limited to, sheets, mattresses, in-soles of shoes, socks, gloves, seat cushions, seat covers, and the like. A skilled artisan will be able to contemplate other embodiments of pressure monitoring devices in accordance with various principles and aspects of the present disclosure.

Figure 4:
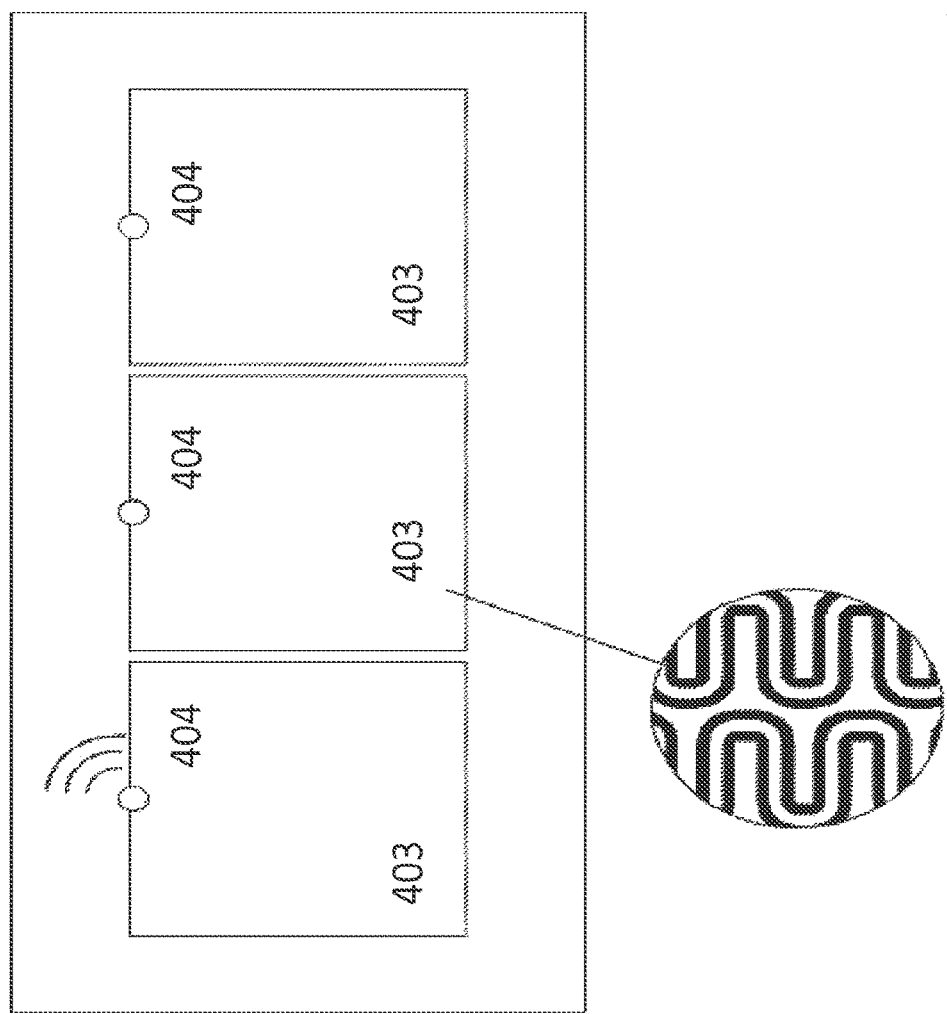
FIG. 4 depicts an embodiment of a pressure monitoring device incorporated in sheet, in accordance with the principles and aspects of the present disclosure.

For example, FIG. 4 depicts an embodiment of a pressure monitoring device wherein the substrate is a sheet (or a mattress cover). 403 schematically depicts an example of placement of fluidic material filled sacs. 404 schematically depicts an example of placement of sensors. Other components of the pressure monitoring device may be suitably placed by one skilled in the art in accordance with various aspects and principles disclosed herein.

One advantage of such a device is that the sensors and associated electronics may be located visibly, hidden away from the measurement area, or can be removable. This means that the sensors and associated electronics can be removed, to facilitate cleaning, including the machine-washing of the device.

In one embodiment, a pressure monitoring system may include a device comprising: (i) a substrate having a contact surface for contacting a user; (ii) one or more fluidic material filled sacs associated with the contact surface of the substrate, and (iii) one or more sensors in communication with the one or more fluidic material filled sacs. The sacs contain a fluidic material configured to transmit pressure. The fluidic material is further configured to be shock-absorbing and pressure-relieving such that the fluidic material is displaceable by an action of the user contacting the contact surface causing the pressure in the fluidic material to be redistributed. The one or more sensors are adapted to measure changes in pressure in the one or more fluidic material filled sacs. The one or more sensors are in communication with at least one transmitter adapted to transmit a measurement by the one or more sensors. The system further includes a controller configured to transmit and/or receive signals to and from the one or more sensors corresponding to the measured changes in pressure, and a user feedback device in communication with the controller. The user feedback device is configured to provide an indication to a user based on the measured changes in pressure.

In some embodiments, the at least one transmitter is adapted to transmit wireless signals using technologies such as, for example, Radio Frequency communication (RF), Near Field Communication (NFC), Bluetooth, Bluetooth low energy (BLE), and the like. The controller is adapted to transmit and/or receive signals compatible to the transmitter.

Receiver containing electronics and user feedback device as display, speakers, and/or an LED light need not be placed on the substrate. These can be placed anywhere on the user interface device or used in the immediate vicinity of the substrate, thereby avoiding placement of hard materials at sites that have high risk of forming pressure ulcers. Additionally, the signal and the power cable may be completely avoided by the sensors and electronics to wirelessly transmit data from the recorded measurement range to the remote receiver, which can be placed at a place on the device or in the vicinity of the latter.

In various embodiments, the user feedback device may be configured to provide an indication or an alert to a user and/or a caregiver attending to the user if the pressure information indicates a pressure in excess of a pre-determined threshold and/or for a duration longer than a pre-determined period of time. The threshold pressure and period of time may be determined by the user and/or the caregiver based on factors such as, for example, age, sex, weight, blood pressure, and/or other factors relating to the user that determine the user's risk of contracting pressure ulcers.

Figure 5:
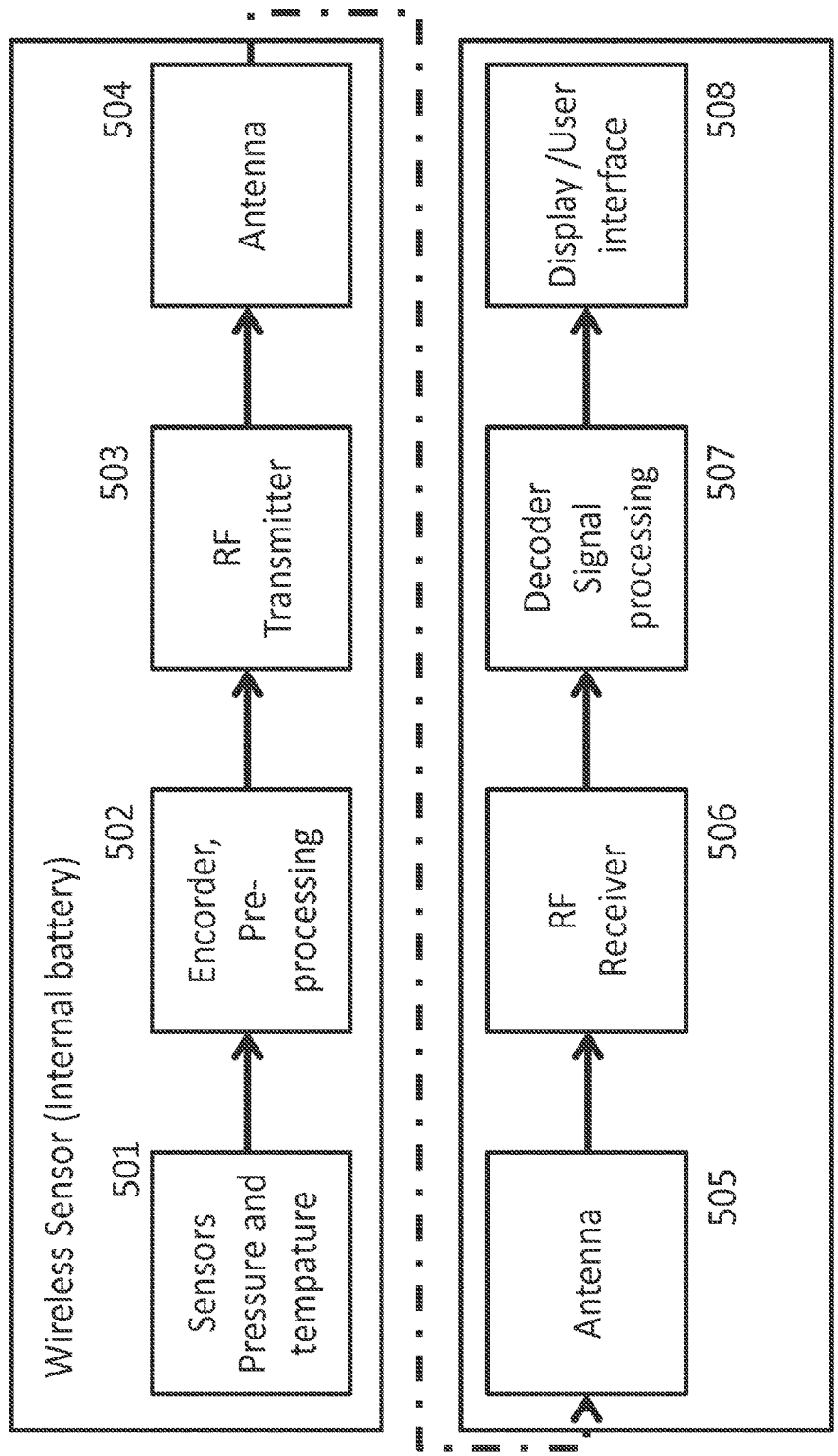
FIG. 5 depicts an embodiment of a wireless pressure monitoring system, in accordance with the principles and aspects of the present disclosure.

FIG. 5 depicts the flow of signals in a wireless pressure monitoring system, in accordance with the principles and aspects of the present disclosure. The embodiment depicted in FIG. 5 includes a temperature sensor to account for pressure changes due to temperature changes. At 501 temperature and pressure data is measured using one or more sensors. This data is encoded and preprocessed at 502 and delivered to the RF transmitter at 503. At 504, the antenna of the RF transmitter transmits pre-processed pressure and temperature data as an RF signal which is received, at 505, by the antenna of the RF receiver. The RF receiver, at 506, delivers the signal to the controller. At 507, the controller decodes the pressure and temperature data, performs additional signal processing (if required) and delivers it to the user feedback device. At 508, the user feedback indicates the temperature and pressure data to the user.

In various embodiments, the controller and the user feedback device may be incorporated in a single device such as, for example, a smartphone, a laptop computer, a tablet computer, a dedicated handheld device, and the like. The user feedback device may indicate a feedback using, for example, audio, audiovisual, visual, or haptic signals.

Various portions of electronics used in the system of the embodiment described with respect to FIG. 5 may be powered using an internal battery. For example, a battery may be disposed in one of the fluidic material filled sacs and be connected to the one or more sensors and the RF transmitter. The energy required for preforming the pressure and/or temperature measurements (as well as other measurements where applicable) as well as for encoding and pre-processing the measurement data may be provided by such a battery. Furthermore, such a battery may also provide energy required by the RF transmitter for transmitting the pressure and temperature data (as well as other data where applicable). Such embodiments may provide continuous real-time data from the measurements. However, such embodiments may be limited in time of use by failure of the internal battery which may need to be replaced periodically and may increase the operating costs. In some other embodiments, a connection lead (not shown) may be provided to the sensor and/or the RF transmitter from outside the substrate. This connection lead may be used to provide energy (using a battery or any other source of electricity). In yet other embodiments, the system may be modified to work without an internal battery.

Figure 6:
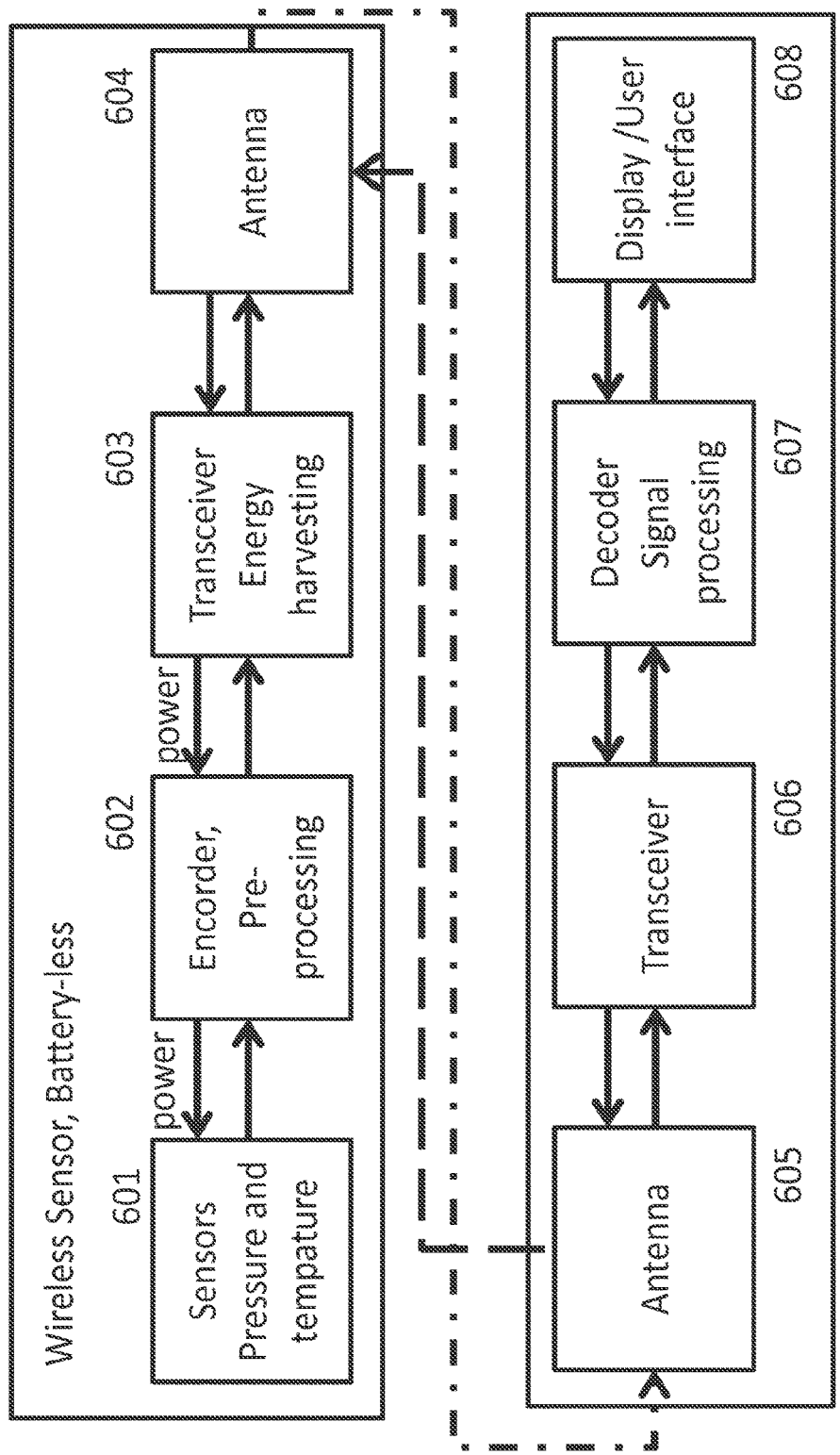
FIG. 6 depicts an embodiment of a battery-less wireless pressure monitoring system, in accordance with the principles and aspects of the present disclosure.

In one embodiment, as depicted in FIG. 6, the system lacks an internal battery used to power the sensors and the RF transmitter. In such an embodiment, the one or more sensors are connected to an RF transceiver which is enabled to harvest energy from a received RF signal. This energy is used to power the sensor(s) to allow the sensor(s) to perform the desired measurements. Alternatively, such an embodiment may use a passive RF tag.

FIG. 6 depicts an embodiment of a battery-less wireless pressure monitoring system, in accordance with the principles and aspects of the present disclosure. At 608, a user or a caregiver requests, through the user feedback device, for pressure and/or temperature data. The request is transmitted through the controller, to the RF transmitter (through 607, 606, 605, and 604, indicated by arrows pointing left). At 603, the RF transceiver harvests energy from the signal it receives and powers the encoder and the sensor(s) (as indicated by the arrows pointing left and labeled power). At 601 temperature and pressure data is measured using one or more sensors. This data is encoded and preprocessed at 602 and delivered to the RF transmitter at 603. At 604, the antenna of the RF transmitter transmits pre-processed pressure and temperature data as an RF signal which is received, at 605, by the antenna of the RF receiver. The RF receiver, at 606, delivers the signal to the controller. At 607, the controller decodes the pressure and temperature data, performs additional signal processing (if required) and delivers it to the user feedback device. At 608, the user feedback indicates the temperature and pressure data to the user.

FIG. 7 depicts an embodiment with a radio frequency transmitter is also used a pressure sensor, in accordance with the principles and aspects of the present disclosure. In an embodiment, a pressure sensor consists of one or more of the passive or active RF tags that can be embedded in a fluidic material filled sac for radio communication and for measuring both static and dynamic pressure changes. When load on the fluidic material filled sac increases, the antenna embedded in the fluidic material filled sac gets stretched resulting in a change in the antenna's detectable complex resistance. This can be used to measure the change in pressure experienced by the fluidic material filled sac.

The devices and systems described herein open new possibilities for a person to monitor problem areas on the body continuously in his daily life, which in turn opens up new opportunities for long-term monitoring of chronic wounds.

Figure 8:
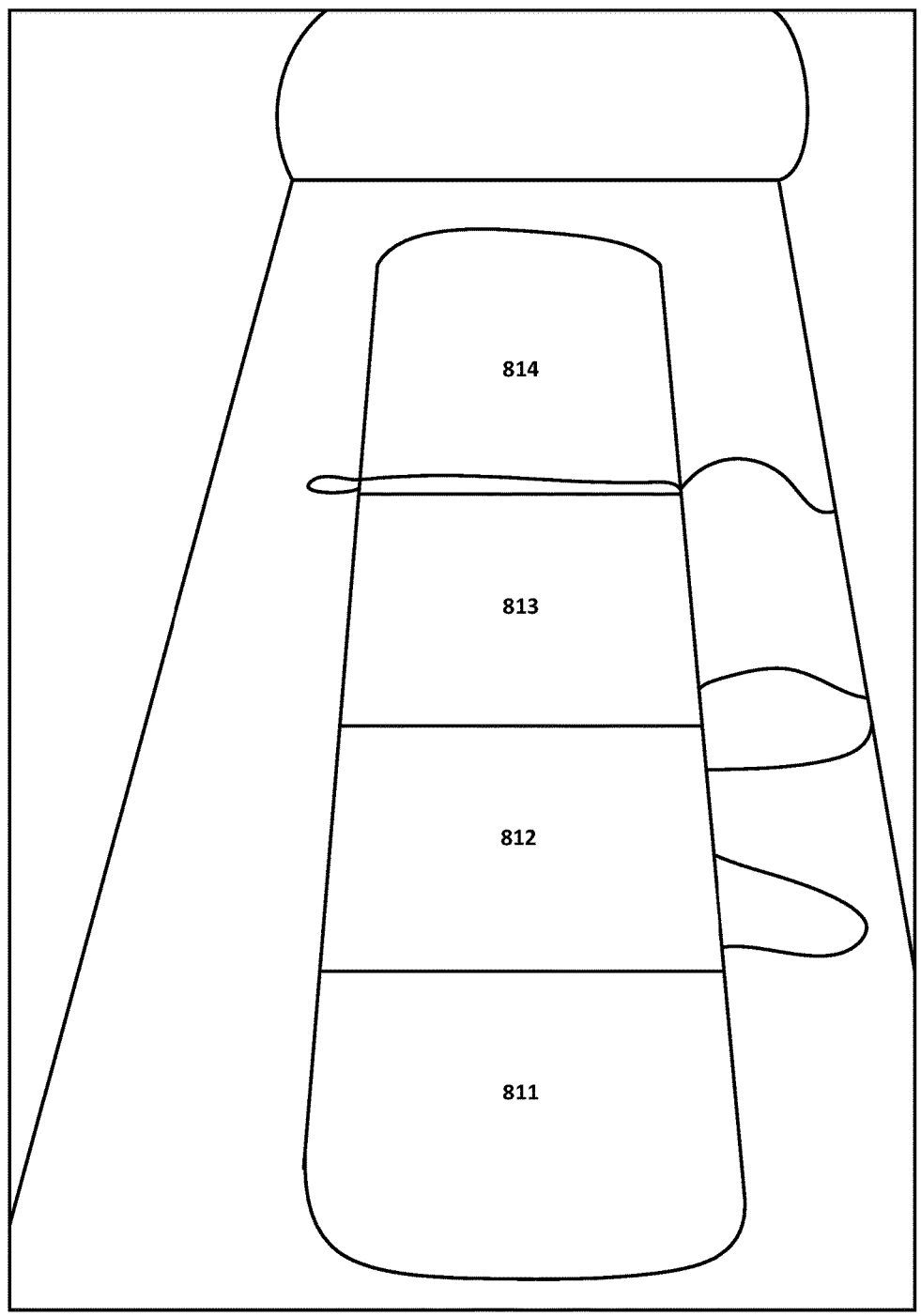
FIG. 8 depicts a photograph of a working prototype of a pressure monitoring system, in accordance with the principles and aspects of the present disclosure.

FIG. 8 depicts a photograph of a working prototype of a pressure monitoring system, in accordance with the principles and aspects of the present disclosure. The photograph shows a sheet. Each of the 4 areas (811, 812, 813 and 814) of interest on the sheet can by monitored independently with a sensor. The pressure and temperature readings can be wirelessly transmitted to a receiver for decoding and further processing. It is a short range wireless application where the transmitter and receiver are separated by a distance of 1 to 50 meter.

In an embodiment, a method of monitoring pressure on a portion of a user's body may include measuring pressure exerted by a portion of a subject's body on one or more fluidic material filled sacs associated with a substrate having a contact surface for contacting with the portion of the subject's body to provide a pressure information, and transmitting the pressure information to a receiving station. The pressure information is used to indicate a pressure in excess of a predetermined threshold using one or more of audio, visual, audiovisual or haptic signal.

The predetermined threshold may be set by the user and/or the caregiver depending on the age, sex, weight, blood pressure, and/or other factors of the user that determine the user's risk of contracting pressure ulcers. Alternatively, a caregiver may provide such recommendation based on such or other factors deemed relevant by the caregiver.

In various embodiments, the method may be executed using the devices or systems described herein. For example, measuring pressure exerted by a user's foot may be performed using the sock described herein. Furthermore, the sock may also be used to transmit the pressure information to the controller or a receiving station of a system described herein. Likewise, in other embodiments, a user feedback device of a system described herein with reference to FIG. 8 may provide the user and/or caregiver with an indication about the excess pressure on portions of a quadriplegic patent's back.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples can be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

Embodiments illustrating the devices, methods and systems described herein may be further understood by reference to the following non-limiting examples:

Example 1: A Sock for Wirelessly Monitoring Pressure on a Foot

FIG. 1 shows a sock for wirelessly monitoring pressure on the foot of a patient. The sock can be made from a suitable textile fabric material such as nylon, spandex, silk, wool, cotton, polyester, and the like, or a combination thereof. A cushioning case or a pouch is stitched to the underside of the sock. The case or pouch is shaped to match the shape the underside of the sock such that a user's foot is completely cushioned by the pouch when the user wears the sock. The pouch is made from substantially the same textile fabric material as the sock. Fluidic material filled sacs made of silicone and filled with air are placed inside the pouch. The fluidic material filled sacs are provided in a meandering pattern (refer to FIG. 1) such that substantially the entire underside of the user's foot resides on at least a portion of the meandering pattern at all times while the user is wearing the sock.

An RF antenna acting as a pressure sensor is placed on the underside of one of fluidic material filled sacs such that the pressure sensor resides directly under heel of the user. A removable battery is provided for powering the RF antenna. The battery may be placed away from the underside of the foot, for example, in the sock near the ankle of the user. A wired connection may be provided from the battery to the RF antenna. A software application (App) on a smartphone communicates with the RF antenna to provide the user with a measurement of pressure on the foot on which the sock is worn. The App is configured to alert the user if the pressure is higher is normal for an extended period of time.

Example 2: Monitoring Pressure on a Foot of a Patient

A patient suffering from diabetic peripheral neuropathy in her feet is provided with a sock of Example 1. When the patient wears the sock, the fluidic material filled sacs act to cushion the foot of the patient on which the sock is worn. When the patient is in a position which exerts excess pressure on a portion of the foot, the fluidic material filled sacs under that portion of the foot redistribute the pressure throughout the surface of the foot. Additionally, the RF antenna and the pressure sensor measure the change in pressure and transmit to the smartphone application provided to the patient. The smartphone application alters the patient about the excess pressure, prompting her to change the position of her foot.

Example 3: A Sheet for Wirelessly Monitoring Pressure on the Backside of a Bed-Bound Patient FIG. 8 shows a working prototype of a sheet for wirelessly monitoring pressure on the back of a bed-bound patient, e.g., a comatose patient or a quadriplegic patient. The sheet consists of 4 distinct compartments (811-814). Each of the compartments can be made from a suitable textile fabric material such as cotton, polyester, and the like, or a combination thereof. The sheet has a length and width sufficient to extend along substantially the entire back portion of a bed-bound patient, i.e., from head to feet, such that a patient lying with their back down would cover at least a portion of the sheet. The compartments may be sized such that the patient's head and neck rest on compartment 811, the patient's upper back rests on compartment 812, the patient's lower back and hind-quarters rest on compartment 813, and the patient's legs rest on compartment 814. Inside each compartment is placed a pouch containing fluidic material filled sacs filled with silicone. The fluidic material filled sacs are provided in a meandering shape. The pouch extends substantially the entire length and width of each of the compartments.

An RF antenna acting as a pressure sensor is placed substantially at the center of each of the pouches inside and under the fluidic material filled sacs. A removable battery or other similar power source is provided for powering the RF antenna. The battery may be placed away from the portion of the compartment that is contact with the body of the patient. A wired connection may be provided from the battery to the RF antenna. A software application on a bedside monitoring device communicates with the RF antenna to provide the patient and/or a caregiver with a measurement of pressure on backside of the patient. The software application is configured to alert the patient and/or the caregiver if the pressure is higher is normal for an extended period of time.

Example 4: Monitoring the Pressure on the Backside of a Bed-Bound Patient

A comatose patient is provided with a sheet of Example 3. The patient lays backside-down on the sheet such that the fluidic material filled sacs act to cushion the backside of the patient. When the patient is in a position which exerts excess pressure on any portion of the patient's body resting on one of the compartments, e.g., a portion upper back near the scapula, the fluidic material filled sacs under that portion of the body redistribute the pressure throughout compartment on which that portion rests. Additionally, the RF antenna and the pressure sensor measure the change in pressure and transmit to the smartphone application provided to the patient. If the pressure has not been relieved over a predetermined length of time, the smartphone application alters the caregiver about the static excess pressure, prompting her to change the patients' position.

What is claimed is:

1. A device comprising:
   a substrate having a contact surface for contacting a user;
   one or more sacs associated with the contact surface of the substrate, the one or more sacs containing a material configured to transmit pressure and the material is configured to be shock-absorbing and pressure-relieving such that the material is displaceable by an action of the user contacting the contact surface causing the pressure in the material to be redistributed; and
   one or more sensors in communication with the one more sacs, wherein the one or more sensors comprises an RFID tag, the RFID tag comprising a microchip, an antenna, and a pressure sensor, and wherein the pressure sensor comprises an object that exhibits a change in electrical resistance or capacitance under deformation of the object.

2. The device of claim 1, further comprising at least one transmitter in communication with the one or more sensors and adapted to transmit a measurement by the one or more sensors to a remote receiver.

3. The device of claim 1, wherein the one or more sensors are further adapted to measure one or more of temperature, humidity or acidity and changes thereto in the one or more sacs.

4. The device of claim 1, wherein the one or more sensors are disposed on an outer surface of the one more sacs.

5. The device of claim 1, wherein the one or more sensors are associated with the contact surface of the substrate.

6. The device of claim 1, wherein the one or more sensors is embedded in the material of the one or more sacs.

7. The device of claim 2, wherein the at least one transmitter is further adapted to receive signals from an external device.

8. The device of claim 1, wherein the one or more sacs are disposed in a meandering pattern.

9. A system comprising: a device comprising:
   a substrate having a contact surface for contacting a user; and
   one or more sacs associated with the contact surface of the substrate, the sacs containing a material configured to transmit pressure and the material is configured to be shock-absorbing and pressure-relieving such that the material is displaceable by an action of the user contacting the contact surface causing the pressure in the material to be redistributed,
   one or more sensors in communication with the one more sacs, wherein the one or more sensors comprises an RFID tag, the RFID tag comprising a microchip, an antenna, and a pressure sensor, and wherein the pressure sensor comprises an object that exhibits a change in electrical resistance or capacitance under deformation of the object;
   a controller configured to communicate with the one or more sensors corresponding to the measured changes in pressure; and
   a user feedback device in communication with the controller, the user feedback device configured to provide an indication to a user based on the measured changes in pressure.

10. The system of claim 9, wherein the one or more sensors are in communication with at least one transmitter.

11. The system of claim 9, wherein the user feedback device is configured to provide indication to the user using one or more of audio, visual, audiovisual, or haptic signals.

12. The system of claim 10, wherein the at least one transmitter is further adapted to receive signals from the controller.

13. The system of claim 9, wherein the one or more sensors are further adapted to measure one or more of temperature, humidity or acidity and changes thereto in the one or more sacs.

14. The system of claim 9, wherein the one or more sensors are disposed on an outer surface of the one more sacs.

15. The system of claim 9, wherein the one or more sensors are associated with the contact surface of the substrate.

16. The system of claim 9, wherein the one or more sensors is embedded in the material of the one or more sacs.

17. The system of claim 9, wherein the one or more sacs disposed in a meandering pattern.

18. A method comprising:
   measuring pressure, using at least one sensor comprising an RFID tag, exerted by a portion of a subject's body on one or more sacs associated with a substrate having a contact surface for contacting with the portion of the subject's body to provide pressure information, the RFID tag comprising a microchip, an antenna, and a pressure sensor, the pressure sensor comprising an object that exhibits a change in electrical resistance or capacitance under deformation of the object;
   transmitting the pressure information to a receiving station via a transmitter in communication with the at least one sensor; and
   providing an indication to a user via a user feedback device based on the pressure information,
   wherein the pressure information indicates, using one or more of audio, visual, audiovisual or haptic signal, a pressure in excess of a predetermined threshold.

19. The method of claim 18, wherein the one or more sacs contain a material configured to transmit pressure and the material is configured to be shock-absorbing and pressure-relieving such that the material is displaceable by an action of the user contacting the contact surface causing pressure in the material to be redistributed.

20. The method of claim 19, further comprising:
   measuring one or more of temperature, humidity or acidity and changes thereto in the one or more sacs using one or more sensors;
   transmitting the measured temperature, humidity or acidity and changes thereto to the receiving station; and
   providing an indication to the user via the user feedback device based on the measured temperature, humidity or acidity information.

* * * * *